(12) United States Patent
Lagerstedt-Eidrup et al.

(10) Patent No.: US 8,283,515 B2
(45) Date of Patent: Oct. 9, 2012

(54) ABSORBENT ARTICLE CONTAINING A SKIN CONDITIONING AGENT

(75) Inventors: Marie-Louise Lagerstedt-Eidrup, Billdal (SE); Anne Farbrot, Askim (SE); Bo Runeman, Jonsered (SE)

(73) Assignee: SCA Hygiene Products AB, Göteborg (SE)

(*) Notice: Subject to any disclaimer, the term of this patent is extended or adjusted under 35 U.S.C. 154(b) by 1825 days.

(21) Appl. No.: 10/427,980

(22) Filed: May 2, 2003

(65) Prior Publication Data

US 2003/0208173 A1    Nov. 6, 2003

Related U.S. Application Data

(60) Provisional application No. 60/377,213, filed on May 3, 2002.

(51) Int. Cl.
*A61F 13/15* (2006.01)
*A61F 13/00* (2006.01)
*A61L 11/00* (2006.01)

(52) U.S. Cl. ........ 604/367; 604/359; 604/360; 604/364; 602/48; 602/49; 602/50; 602/51; 424/76.5

(58) Field of Classification Search ........... 604/364, 604/368–369, 359–360, 367; 602/48–51; 424/76.5
See application file for complete search history.

(56) References Cited

U.S. PATENT DOCUMENTS

| | | | | |
|---|---|---|---|---|
| 3,901,240 A | * | 8/1975 | Hoey | 604/364 |
| 4,026,292 A | * | 5/1977 | Hutchins et al. | 604/363 |
| 5,051,259 A | | 9/1991 | Olsen et al. | |
| 5,147,344 A | | 9/1992 | Sachau et al. | |
| 5,750,585 A | * | 5/1998 | Park et al. | 521/143 |
| 5,814,649 A | | 9/1998 | Amano et al. | |
| 5,843,267 A | | 12/1998 | Cashaw et al. | |
| 5,961,504 A | * | 10/1999 | Gross | 604/358 |
| 6,060,079 A | * | 5/2000 | Freeman et al. | 424/449 |
| 6,136,873 A | * | 10/2000 | Hahnle et al. | 521/62 |
| 6,143,946 A | * | 11/2000 | Docter | 602/41 |
| 6,166,285 A | * | 12/2000 | Schulte et al. | 604/364 |
| 6,245,410 B1 | | 6/2001 | Hähnle et al. | |
| 6,296,862 B1 | * | 10/2001 | Paul et al. | 424/402 |
| 6,455,600 B1 | | 9/2002 | Hähnle et al. | |

(Continued)

FOREIGN PATENT DOCUMENTS

DE    10257002 A1 *  6/2003

(Continued)

OTHER PUBLICATIONS

Russian Office Action for RU application No. 2004135320/14(038425).

(Continued)

*Primary Examiner* — Jacqueline F. Stephens

(74) *Attorney, Agent, or Firm* — Buchanan Ingersoll & Rooney PC

(57) ABSTRACT

An absorbent article such as a diaper, pant diaper, adult incontinence guard, sanitary napkin and the like contains a skin conditioning agent in at least a portion of the article so as to be transferable to the skin of the wearer. The skin conditioning agent is contained in a hydrogel foam material (9; 19; 20) intended to be applied in skin contact with the wearer, either directly or indirectly via a liquid permeable material (2).

5 Claims, 2 Drawing Sheets

U.S. PATENT DOCUMENTS 6,476,288 B1 * 11/2002 VanRijswijck et al. ....... 604/364

FOREIGN PATENT DOCUMENTS

| | | |
|---|---|---|
| EP | 0 614 697 | 9/1994 |
| EP | 0858 478 B | 5/1997 |
| EP | 1035818 A | 9/2000 |
| EP | 1 149 846 | 10/2001 |
| RU | 2060035 C1 | 5/1996 |
| WO | 89/05619 | 6/1989 |
| WO | 96 11682 | 4/1996 |
| WO | 96/16682 | 6/1996 |
| WO | 97/17397 | 5/1997 |
| WO | 97 31600 | 9/1997 |
| WO | 97 38735 | 10/1997 |
| WO | 99 22684 | 5/1999 |
| WO | 99 44648 | 9/1999 |
| WO | 99 61518 | 12/1999 |
| WO | 00 52087 | 9/2000 |
| WO | 01 00129 | 1/2001 |

OTHER PUBLICATIONS

Translation of Russian Office Action for RU application No. 2004135320/14(038425).

* cited by examiner

ABSORBENT ARTICLE CONTAINING A SKIN CONDITIONING AGENT

CROSS-REFERENCE TO RELATED APPLICATION

This application claims priority to U.S. provisional Application No. 60/377,213, filed May 3, 2002, entitled "Absorbent Article Containing a Skin Conditioning Agent," the content of which is hereby incorporated in its entirety and relied upon.

TECHNICAL FIELD

The present invention refers to an absorbent article such as a diaper, pant diaper, incontinence pad, sanitary napkin, panty liner and the like. More particularly, the present invention refers to absorbent articles having a skin treating composition applied on at least a portion thereof, said composition being transferable to the skin of the wearer by normal contact and wearer motion and/or body heat.

BACKGROUND OF THE INVENTION

A number of attempts have been made to produce skin-friendly absorbent articles. The surfaces intended to bear against the skin of the user during use of the article, especially the liquid-permeable topsheet of the article, can be coated with a skin-conditioning agent. This is disclosed in WO 96/16682, e.g., which describes a diaper having a lotioned topsheet.

WO 99/22684 discloses a web material having two or more skin care compositions. The web is attached at different points of a diaper, e.g., the topsheet, the liquid barriers or the like which are in direct contact with the skin of the wearer.

Hydrogel foams are known as absorbent elements in absorbent articles. EP-B-0 858 478 and WO-A-00/52087, e.g., describe water-absorbent, predominantly open-celled foams based on crosslinked acid-functional monomers. They are prepared by foaming a polymerizable aqueous mixture containing at least 50 mol % neutralized acid-functional monoethylenically unsaturated monomers, crosslinkers and at least one surfactant and subsequently polymerizing the foamed mixture. The foaming of the polymerizable mixture can be effected, e.g., by dispersing fine bubbles of a gas, which is inert toward free radicals or by dissolving such a gas under elevated pressure in the polymerizable mixture and decompressing the mixture. The water content of the foams is adjusted to 1-60% by weight, e.g. The foams can optionally be subjected to surface postcrosslinking by spraying a crosslinker onto the foamed material or immersing the foam therein and heating the crosslinker-laden foam to a higher temperature. The foams are used, e.g., in hygiene articles to acquire, distribute and store body fluids.

WO-A-99/44648 likewise discloses predominantly open-celled foams based on crosslinked acid-functional monomers where at least 20 mol % of the acid-functional monomers are neutralized with tertiary alkanolamines and/or the free acid groups of the hydrogel foam are at least 20 mol % neutralized with at least one alkanolamine after polymerisation The hydrogel foams neutralized with alkanolamines are tacky. The tackiness is fully removable by powdering with finely divided powders such as finely divided silicon dioxide, talcum, silicates or starch.

WO-A-97/31600 discloses an absorbent element for use in hygiene or sanitary articles wherein a plurality of elements of a superabsorbent foam are arranged on a support in a grid pattern at such distances that the elements in the swollen state touch at their peripheries. For example, a monomer foam can be applied to the support in the desired grid pattern and then polymerized or separately prepared foam elements can be fixed on the support in the desired grid pattern by chemical or physical means.

SUMMARY

It is an object of the present invention to provide an absorbent article containing a skin conditioning agent providing improved comfort and skin care characteristics. It has been found that this object is achieved, according to various embodiments of the invention, by the fact that the skin conditioning agent is contained in a hydrogel foam material intended to be applied in skin contact with the wearer, either directly or indirectly via a liquid permeable material.

The hydrogel foam material containing the skin conditioning agent may be located as an absorbent component in the absorbent body of the article. It may be located alternatively or additionally in areas of the article intended to be in contact with at least one of the following body portions of the wearer: groins, buttocks, genitalia, hips.

Alternatively or additionally, the hydrogel foam material containing the skin conditioning agent may form part of or constitute elastic members in the article. It may also be applied on the body-contacting surface of a belt on a diaper, with the belt being intended to be fastened around the waist of the wearer.

The hydrogel foam material may be applied as strips intended to create leakage barriers in the article. It may also be applied to form a feces barrier in the article. In the latter case, it preferably contains an enzyme inhibitor, especially a lipase and/or protease inhibitor.

According to one embodiment, the hydrogel foam material is formed from water absorbent crosslinked polymer foams containing units derived from monoethylenically unsaturated acids, such as acrylic acid.

The skin conditioning agent used is adapted for preventing, relieving or healing dermatitis.

The skin conditioning agent may comprise one or more of the following substances: emollients, pH-regulating substances, antimicrobial substances, glucocortoids, antiviral agents, enzyme inhibitors anti-inflammatory substances.

DETAILED DESCRIPTION OF THE PREFERRED EMBODIMENTS

The term "absorbent article" refers to products that are placed against the skin of the wearer to absorb and contain body exudates, like urine, faeces and menstrual fluid. The invention mainly refers to disposable absorbent articles, which means articles that are not intended to be laundered or otherwise restored or reused as an absorbent article after use. Examples of disposable absorbent articles include feminine hygiene products such as sanitary napkins, panty liners and sanitary panties; diapers and pant diapers for infants and incontinent adults; incontinence pads; diaper inserts; and the like.

Figure 1:
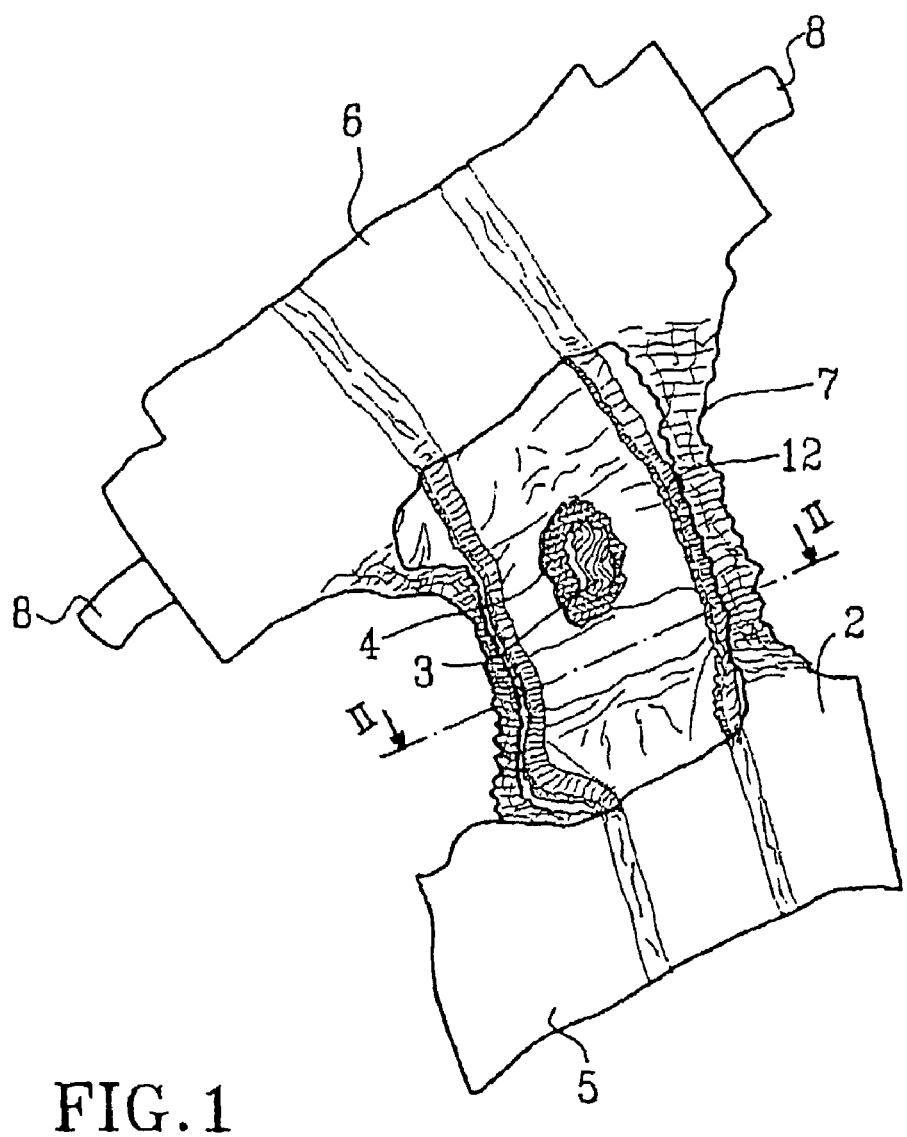
FIG. 1 is a perspective view of an embodiment of an absorbent article in the form of a diaper.
Figure 2:
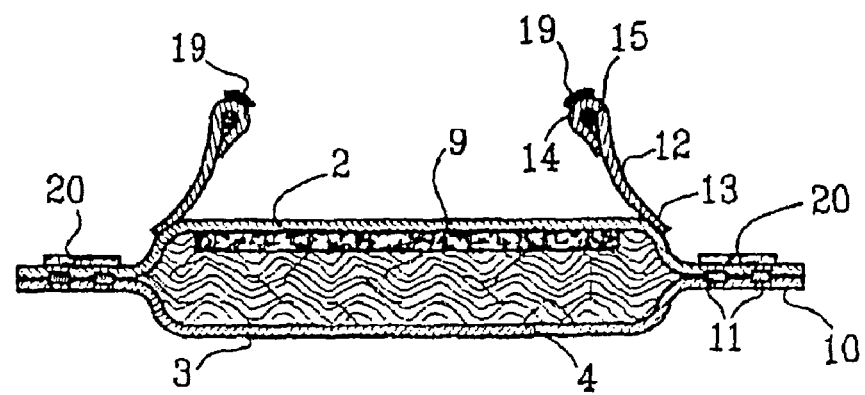
FIG. 2 is a fragmentary sectional view through an absorbent article.

FIGS. 1 and 2 show an embodiment of a diaper 1 for an infant or an incontinent adult, said diaper typically comprises a chassis comprising a liquid permeable topsheet 2, a liquid impermeable backsheet 3 and an absorbent body 4 enclosed therebetween. The liquid permeable topsheet 2 can consist of a nonwoven material, e.g., spunbonded, meltblown, carded, hydroentangled, wetlaid, etc. Suitable nonwoven materials can be composed of natural fibers, such as woodpulp or cotton fibers, manmade fibers, such as polyester, polyethylene, polypropylene, viscose, etc. or from a mixture of natural and manmade fibers. The topsheet material may further be composed of tow fibers, which may be bonded to each other in a bonding pattern, as, e.g., disclosed in EP-A-1 035 818. Further examples of topsheet materials are porous foams, apertured plastic films etc. The materials suited as topsheet materials should be soft and non-irritating to the skin and be readily penetrated by body fluid, e.g., urine or menstrual fluid.

The liquid impermeable backsheet 3 may consist of a thin plastic film, e.g., a polyethylene or polypropylene film, a nonwoven material coated with a liquid impervious material, a hydrophobic nonwoven material, which resists liquid penetration or laminates of plastic films and nonwoven materials. The backsheet material may be breathable so as to allow vapour to escape from the absorbent core, while still preventing liquids from passing through the backsheet material.

The topsheet 2 and the backsheet material 3 have a somewhat greater extension in the plane than the absorbent body 4 and extends outside the edges thereof. The layers 2 and 3 are connected to each other within the projecting portions thereof, e.g., by gluing or welding by heat or ultrasonic. The topsheet and/or the backsheet may further be attached to the absorbent core by any method known in the art, such as adhesive, heatbonding, etc. The absorbent core may also be unattached to the topsheet and/or the backsheet.

The absorbent body 4 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body. It is also common to have absorbent bodies comprising layers of different material with different properties with respect to liquid acquisition capacity, liquid distribution capacity and storage capacity. This is well-known to the person skilled in the art and therefore does not have to be described in detail. The thin absorbent bodies, which are common in, e.g., baby diapers and incontinence guards, often comprise a compressed mixed or layered structure of cellulosic fluff pulp and superabsorbent. The size and absorbent capacity of the absorbent core may be varied to be suited for different uses such as baby diapers, adult incontinence diapers and pads, pant diapers, panty liners, sanitary napkins, etc.

The absorbent core 4 or part of the absorbent core may also comprise a hydrogel foam material of the kind, which will be described in greater detail below. In FIG. 2, it is indicated that an upper layer of the absorbent core, the liquid acquisition layer 9, consists of a hydrogel foam material.

The diaper disclosed in FIG. 1 is intended to enclose the lower part of the wearer's trunk like a pair of absorbent pants. It comprises a front portion 5 intended during use to be worn on the front part of the user's body, a rear portion 6 intended during use to be worn on the rear part of the user's body, and a more narrow crotch portion 7 located between the front and rear portions intended to be worn in the crotch part of the user between the legs. The front portion 5 is provided with a pair of adhesive tape tabs 8 or other type of attachment means such as hook-and-loop type fasteners.

The diaper comprises elasticised side flaps 10 forming leg openings. Elastification is provided by elastic members 11 secured between the topsheet and backsheet in the side flap region 10. The diaper disclosed in FIGS. 1 and 2 further comprises elastic barrier flaps 12 having a proximal edge 13 and a distal edge 14 and elastic member 15 spacing the distal edge 14 away from the topsheet. These barrier flaps 12 form leakage barriers and are at their proximal edges 13 secured to the topsheet 2 close to the lateral edges of the absorbent core 4 either in the area of the side flaps 10 or above the absorbent core 4.

The diaper may further comprise elasticised waist feature in the form of elastic members extending in the transverse direction of the article in the waist portion thereof.

Figure 3:
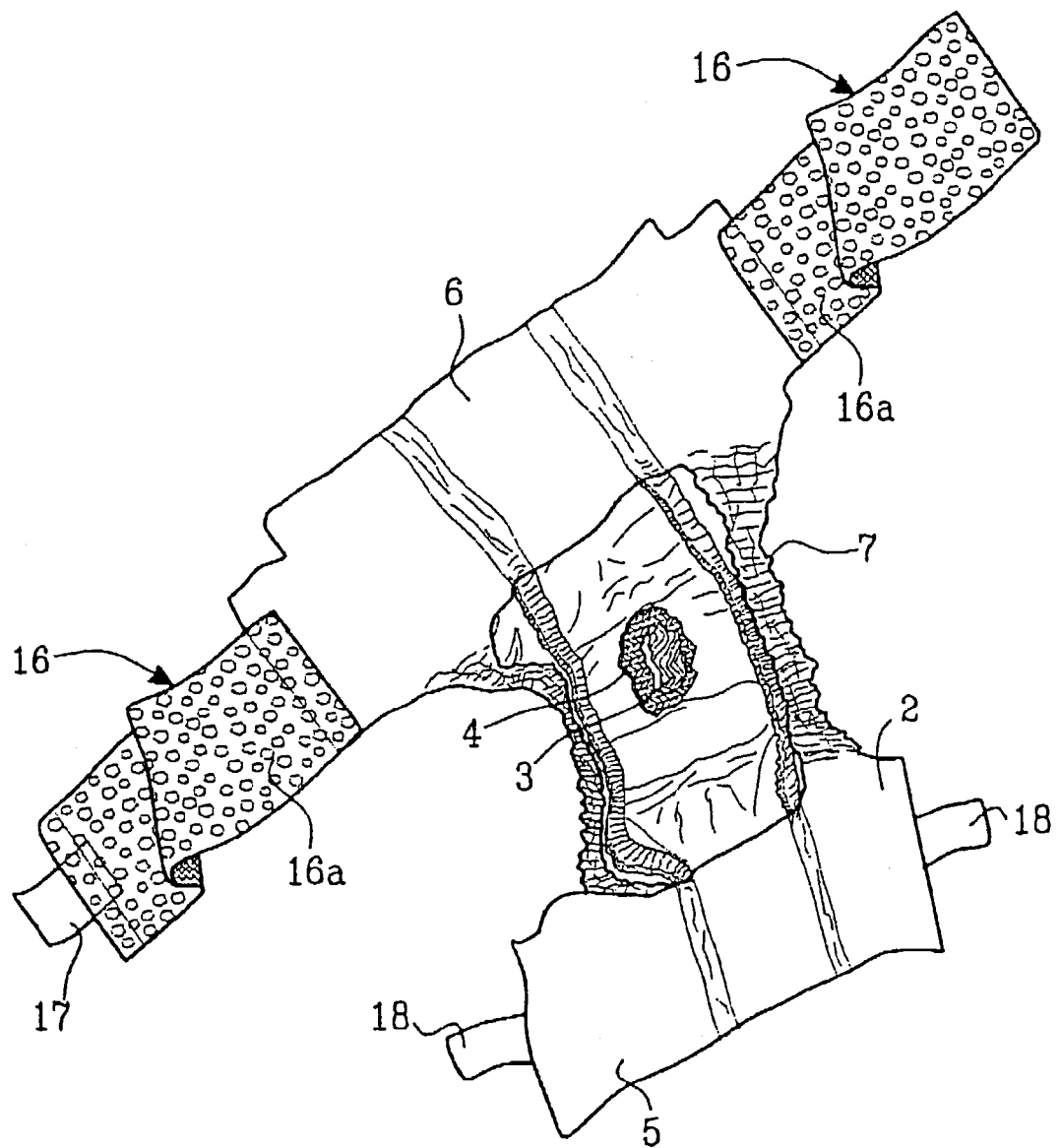
FIG. 3 is a perspective view of a further embodiment of an absorbent article in the form of a belted diaper.

In a further embodiment, shown in FIG. 3, the diaper comprises belt portions 16 attached to the rear portion of the diaper and intended to be fastened together, by fastening means 17, around the waist of the wearer. Fastening means 18 on the front part 5 of the diaper are then attached to the outside of the belt. An example of a belted diaper is shown in FIG. 3 and described in for example WO 01/00129.

It is however understood that the diapers described above and shown in the drawings only represents two non-limiting examples and that the present invention is not limited thereto, but can be used in any type of absorbent articles as defined above.

Diaper Dermatitis

Several factors in combination lead to the development of diaper dermatitis. Wet skin results in chafing and pressure, which more easily wear down the skin. A high moisture content also means that skin penetration by irritant substances can increase, and that bacteria and fungi can thrive. Occlusion of skin and breakdown of urea in the urine to ammonia results in an increase in the pH. The higher pH value leads to that enzymes (lipases and proteases) coming from the intestine, and from the microorganisms in the excrement, can break down the skin to a greater extent. A vicious circle can easily develop in which various factors facilitate and intensify each other.

Dermatitis is best prevented by creating conditions which counteract those factors which create and maintain the process of diaper dermatitis. It should therefore be endeavoured to keep the skin as dry as possible, to air the skin often and to change wet diapers. Mechanical shearing forces should be minimized by choosing materials which are as smooth and soft as possible, and wear between diaper and skin should be minimized. By supplying the skin with a softening and protective lotion or cream, it is further possible to strengthen the barrier against penetration of irritant substances and enzymes. In more serious cases of dermatitis, microorganisms may have infected the damaged skin, and treatment with more active medicines is required. Ointment with cortisone and various fungicidal and bactericidal agents are then used.

Hydrogel Foam Materials

Water-absorbent, predominantly open-celled crosslinked acid-functional addition polymer foams are known from the prior art cited at the beginning, cf. EP-B-0 858 478 page 2 line 55 to page 10 line 54, WO-A-99/44648 page 4 line 41 to page 27 line 42 and WO-A-00/52087 page 5 line 32 to page 28 line 45. They are also known as hydrogel foams and are obtainable for example by first preparing a polymerizable aqueous mixture containing from 10 to 80% by weight of acid-functional monoethylenically unsaturated monomers which are partially neutralized, e.g., at least 20 mol % neutralized, optionally up to 50% by weight of other monoethylenically unsaturated monomers, from 0.001 to 5% by weight of crosslinker, at least one initiator, from 0.1 to 20% by weight of at least one surfactant, optionally a solubilizer and optionally thickeners, foam stabilizers, polymerisation regulators, fillers and/or nucleators.

The polymerizable aqueous mixture is foamed either by dispersing fine bubbles of a gas which is inert toward free radicals or by dissolving an inert gas under a pressure of from 2 to 400 bar and then decompressing the mixture to atmospheric. In either case, the foamed mixture is then in either case polymerized to form a hydrogel foam. This method makes it possible to obtain formed foam articles in any shape, although preference is given to blocks from which foam webs or sheets of, e.g., from 0.5 to 10 mm in thickness can be cut, and also to sheets, webs or films. The surface of these formed articles can then be treated with silicon dioxide and/or surfactants or preferably prior to this treatment subjected to a postcrosslinking operation. To postcrosslink the formed foam articles, they are initially treated with a solution of a crosslinker, e.g., of a polyhydric alcohol such as propylene glycol or butylene glycol, bisepoxides or polyglycidyl compounds, and the crosslinker-solution-treated sheetlike structures formed of predominantly open-celled crosslinked acid-functional addition polymer foams are heated to, e.g., 120° C. to 200° C. to postcrosslink the surface, the crosslinkers reacting with the acid groups of the hydrogel foams to form covalent bonds.

Useful acid-functional monoethylenically unsaturated monomers include, e.g., acrylic acid, methacrylic acid, acrylamidopropanesulfonic acid or mixtures thereof. Particular preference is given to the use of acrylic acid as a monomer to prepare water-absorbent addition polymers. The acid-functional compounds are usually neutralized with the aid of aqueous sodium hydroxide solution or potassium hydroxide solution. Neutralization may also be carried out using sodium silicate. Water-absorbent polymers can also be prepared by polymerizing the acid-functional monomers, e.g., in the presence of natural products such as starch, cellulose, cellulose derivatives or degradation products of starch such as oxidized starch, enzymatically degraded starch or in the presence of acids or bases of destructured starch. Graft polymers are formed. Instead of acid-functional monomers it is also possible to polymerize acrylonitrile or methacrylonitrile in the presence or absence of the above-described natural products and subsequently in either case hydrolyze the nitrile groups to acid groups.

The polymerisation of the acid-functional monomers and also of acrylonitrile and methacrylonitrile is always effected in the presence of at least one crosslinker, one initiator and one surfactant in an aqueous medium. These materials are present in the polymerizable aqueous mixture which is foamed for example by the mechanical foaming method (dispersing of fine bubbles of an inert gas into the polymerizable mixture) or by dissolving for example carbon dioxide in the polymerizable aqueous mixture under a pressure of, e.g., 12 bar and decompressing this mixture to atmospheric. The flowable foam thus prepared can then be transferred, e.g., onto a belt having side walls or into miolds and polymerized into webs, sheets, films or blocks and subsequently dried. The polymerisation is carried out by prior art processes. Depending on the initiator used, it can be effected by raising the temperature, by the action of light (UV rays), by irradiation with electron beams or else by a combination thereof, e.g., by raising the temperature and UV irradiation.

Foam layers up to 1 mm thick are prepared, e.g., by one-sidedly heating or irradiating a polymerizable mixture. To produce sheetlike foam structures more than one centimeter in thickness, the polymerizable mixture is heated by the action of microwaves for preference. Sheetlike structures of foams, e.g., from 1 mm to 5 cm, and preferably up to 2 cm in thickness, are preferably prepared by initiating the polymerisation of the polymerizable foam mixture on both sides, e.g., by heating the mixture on a belt having side walls while at the same time irradiating the foam from above with UV light. The density of the foam changes only little if at all during the polymerisation. The water content of the foams has a major influence on their flexibility. The water content is generally in the range from 1 to 80% by weight and preferably in the range from 5 to 60% by weight.

Foams having particularly high flexibility are obtained when at least 20 mol % of the acid groups of water-absorbent crosslinked acid-functional addition polymer foams have been neutralized with alkanolamines, cf. WO-A-00/52087, page 25 line 1 to page 26 line 10. The degree of neutralization of the carboxyl groups of the hydrogel foams is, e.g., in the range from 40 to 95 mol % and preferably in the range from 55 to 85 mol %. By predominantly open-celled is meant that at least 80% of the hydrogel foam is open-celled. The hydrogel foams are preferably 100% open-celled.

The water-absorbent, predominantly open-celled crosslinked acid-functional polymer foams have for example a density of from 0.001 to 0.9 $g/cm^3$ and preferably of from 0.05 to 0.5 $g/cm^3$, a water absorption capacity of at least 5 g/g, a Free Absorption Rate (FAR) of from 4.0 to 100 g/g sec for a 0.9% by weight aqueous sodium chloride solution and a Vertical Wicking Time (VWT=time for a 0.9% by weight aqueous sodium chloride solution to advance vertically in a foam) of from 0.2 to 120 seconds for a height of 4 cm.

The above-described, sheetlike constructs formed of hydrogel foams may be subjected to a surface postcrosslinking operation on one side or on both sides. The postcrosslinking operation can be carried out not only on the dried but also on the moist hydrogel foam after polymerisation. To prepare a sheetlike structure in a hydrogel foam having a postcrosslinking gradient, the foam is fed as a sheetlike structure. This can be effected, e.g., in the form of individual sheets, films, tapes or other sheetlike geometric forms of varying size. For instance, a polyacrylate foam in the form of an endless roll can be subjected to a surface postcrosslinking operation on one side only, on a moving belt, so that an inhomogeneous postcrosslinking takes place in the z direction, where the x and y directions define the area of the surface.

In the inhomogeneous postcrosslinking operation, the crosslinking reagents are applied only to one surface of hydrogel foam, i.e., compounds having at least two reactive groups capable under suitable conditions, e.g., on heating to not less than 70° C., of reacting with the acid groups of the hydrogel foam. It is also possible in this case to achieve a modification of the inhomogeneous crosslink density by controlling the depthwise penetration of the crosslinker. Suitable crosslinkers combine with the carboxyl groups of the polymer matrix to form covalent or ionic bonds. Such compounds are preferably applied in the form of an aqueous solution to the surface of the sheetlike structure of a hydrogel foam. The aqueous solution can contain, e.g., water-miscible organic solvents, such as alcohols such as methanol, ethanol or isopropanol, acetone, dimethylformamide or dimethyl sulfoxide. Useful crosslinkers include in principle all compounds useful as crosslinkers for preparing hydrogels. Examples of suitable postcrosslinking agents are:

di- or polyglycidyl compounds such as phosphonic acid diglycidyl ether or ethylene glycol diglycidyl ether,
bischlorohydrin ethers of polyalkylene glycols,
alkoxysilyl compounds,
polyaziridines, compounds which contain aziridine units and are based on polyethers or substituted hydrocarbons, e.g., bis-N-aziridinomethane,
polyamines or polyamidoamines or their reaction products with epichlorohydrin,
polyols such as ethylene glycol, 1,2-propanediol, 1,4-butanediol, glycerol, methyltriglycol, polyethylene glycols having an average molecular weight MW, of 200-10,000, di- and polyglycerol, pentaerythritol,
trimethylolpropane, sorbitol, the ethoxylates of these polyols, e.g., glycerol, pentaerythritol and/or trimethylolpropane ethoxylation products containing from 1 to 20 and preferably from 2 to 8 ethylene oxide units per OH group, and also esters thereof with carboxylic acids or carbonic esters such as ethylene carbonate or propylene carbonate,
carbonic acid derivatives such as urea, thiourea, guanidine, dicyandiamide, 2-oxazolidinone and its derivatives, bisoxazoline, polyoxazolines, di- and polyisocyanates,
di- and poly-N-methylol compounds such as methylenebis (N-methylolmethacrylamide) or melamine-formaldehyde resins, compounds having two or more blocked isocyanate groups such as for example trimethylhexamethylene diisocyanate blocked with 2,2,3,6-tetramethyl-4-piperidinone,
solutions of divalent or more highly valent metal salts of which the metal cations can react with the acid groups of the polymer to form ionic or covalent bonds or complexes.

Examples of divalent or more highly valent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Zn^{2+}$, $Zr^{4+}$, $La^{3+}$ and $Ce^{4+}$. Preferred metal cations are $Mg^{2+}$, $Ca^{2+}$, $Ba^{2+}$, $Al^{3+}$ and $Zr^{4+}$. The metal cations may be used alone, mixed with each other, and together with at least one other customary crosslinker (cf. above). Of the metal cations mentioned, all metal salts that possess adequate solubility in the solvent to be used are suitable. Of particular suitability are metal salts with weakly complexing anions such as chloride, nitrate and sulfate. Useful solvents for the metal salts include water, alcohols, acetone, dimethylformamide, dimethyl sulfoxide, and mixtures thereof.

Particularly preferred solvents are water and water-alcohol mixtures such as water/methanol or water/1,2-propanediol.

If necessary, the postcrosslinking operation can be carried out in the presence of acidic catalysts such as p-toluenesulfonic acid, phosphoric acid, boric acid or ammonium dihydrogenphosphate.

Particularly suitable postcrosslinking agents are di- or polyglycidyl compounds such as ethylene glycol diglycidyl ether, the reaction products of polyamidoamines with epichlorohydrin, polyvalent metal cations and 2-oxazolidinone.

In a continuous production process, the crosslinker solution is preferably applied by spraying a solution of the crosslinker, e.g., through parallel connected nozzles which spray onto one surface only of the sheetlike hydrogel foam. The solution of the crosslinker can be applied via any apparatus known to one skilled in the art. It can be augmented, e.g., with compressed air or effected without compressed air. The compressed air is preferably produced using inert carrier gas, for example nitrogen, argon or helium. Furthermore, the area to be impregnated can be determined and set via spray angles. The spray angle can be chosen via electronically adjustable nozzle opening. The setting of the droplet size of the solution to be sprayed can alternatively be effected via the setting of the viscosity of the crosslinker solution and/or via the compressed air. The surface of the sheetlike structure of hydrogel foam can be provided with the crosslinker homogeneously or, as indicated above, inhomogeneously. The crosslinker or a solution of the crosslinker can also, e.g., be printed in the form of a pattern onto the surface of the hydrogel foam or be applied in the form of a pattern in any other way. Similarly, onesided application of the crosslinker is possible using a knife coater.

In one embodiment, the postcrosslinker solution is applied, e.g., in an amount per unit area which should preferably not exceed 0.02 ml/cm². More preferably, the surface has a postcrosslinker solution rate in the range from 0.001 to 0.015 ml/cm² and most preferably in the range from 0.001 to 0.012 ml/cm². This application rate ensures that the depthwise penetration of the postcrosslinker solution does not exceed the thickness of the sheetlike construct of hydrogel foaml so that a postcrosslinking gradient can develop.

Generally, the postcrosslinker solution is applied in such a concentration that the solvent does not account for more than 50% by weight and the crosslinker quantity for not more than 40% by weight, each based on polymer. Preferably the surface receives a solvent quantity in the concentration range from 0.1 to 30% by weight, more preferably in the concentration range from 0.5 to 20% by weight and most preferably in the concentration range from 1 to 10% by weight, each based on polymer. The crosslinker quantity based on polymer foam is, e.g., in the range from 0.1 to 25% by weight, preferably in the range from 0.5 to 10% by weight and mostly in the range from 0.5 to 8% by weight.

The postcrosslinking gradient can be controlled for example by controlling the depthwise penetration of the crosslinker solution via the application rate and crosslinker quantity depending on the layer thickness of the sheetlike hydrogel foam feed. In the case of sheetlike structures, just one or else both of the surfaces of the gel foam may be postcrosslinked. To prepare sheetlike structures having a postcrosslinking gradient between the top surface and the bottom surface, different accounts of crosslinkers must be applied to the top surface and the bottom surface. To prepare a sheetlike structure of a hydrogel foam having a postcrosslinking gradient between top surface and bottom surface, it is also possible to apply at least one crosslinker or a solution, containing at least one crosslinker to the top surface and to the bottom surface of the sheetlike structure in equal amounts. This application is to carry out the postcrosslinking operation and subsequently to split the thus both sidedly surface-postcrosslinked sheetlike structure a single time by, e.g., making a horisontal cut in the z direction of the sheetlike structure. If, for example, the cut is made in the middle of the z direction of the both sidedly postcrosslinked sheetlike structure, it is halved.

After the crosslinker solution has been applied the crosslinker is reacted with the hydrogel foam, e.g., in a downstream drying zone, at from 80° C. to 1900° C. and preferably at from 100° C. to 1600° C. The reaction time is for example in the range from 2 minutes to 6 hours, preferably in the range from 10 minutes to 2 hours and mostly in the range from 10 minutes to 1 hour, during which not only cleavage products but also solvent fractions can be removed. The drying and postcrosslinking operation can also be effected by blowing with a preheated carrier gas.

Sheetlike structures formed of a hydrogel foam can be used in hygiene articles directly or after a surficial postcrosslinking operation, which can be carried out on both sides or preferably on one side, and subsequent treatment with at least one skin conditioning agent as an acquisition layer and/or distribution layer and/or storage layer. In the case of a merely one-sidedly postcrosslinking operation on sheetlike hydrogel foam, there is a crosslink gradient between the upper surface and the lower surface of the sheetlike structure. Such onesidedly crosslinked sheetlike structures formed of hydrogel foams and treated with a skin conditioning agent are preferably used in hygiene articles so that the surface having the higher crosslink density faces the body. Such a structure has distinctly improved properties over homogeneously crosslinked sheetlike samples of the same size which have been subjected to the same treatment with a skin conditioning agent with regard to absorption rate and permeability.

Examples of Skin Conditioning Agents

Useful skin conditioning agents are emollients. Emollients are products which have softening and smoothing properties on the skin. Emollients may also impart general smoothing by flattening the skin's profile. These effects may be simply due to the hydration caused by the occlusive effect of the emollients. Emollients also serve to lubricate the skin's surface and diminish the rough feel associated with the dead cells of the outermost skin layer. An emollient may soften, smoothe, coat, moisturize, lubricate, or cleanse the skin. In general, an emollient may simultaneously accomplish several of these objectives such as smoothing, moisturizing, and lubricating the skin.

Lipophilic emollients include petroleum-based hydrocarbons (e.g., mineral oil, paraffin, isoparaffin, petrolatum), fatty acid esters (e.g., natural animal and plant derived triglycerides, methyl palmitate, methyl stearate, isopropyl laurate, isopropyl palmitate, ethylhexyl palmitate, oleyl oleate, octyl stearate, hexyl laurate, myristyl myristate), alkyl ethoxylates (e.g., lauryl, cetyl and, stearyl ethoxylates), fatty acid ester ethoxylates, fatty alcohols (e.g., octyl dodecanol, hexyl decanol, oleyl alcohol, cetyl alcohol, stearyl alcohol, behenyl alcohol), polysiloxanes (e.g., dimethicone, cetyl dimethicone, cyclomethicone) and mixtures thereof.

A skin conditioning agent with emollient properties may be composed of several different hydrophilic and lipophilic emollients and as a water-in-oil emulsion or an oil-in-water emulsion. The emulsion may be stabilized with an emulsifier. The emulsifier may be of amphoteric, anionic, cationic or nonionic type.

In order to optimize the skin care agent's emollient capacity or technical ability in the foam product, additional components may be added. The additional components may be needed for stabilizing the product, modifying viscosity, regulating the pH, microbial safety (e.g., preservatives), etc.

Useful skin conditioning agents include, e.g., panthenol, collagen, vitamins and proteins. It is also possible to use zinc oxide and metal salts of fatty acids such as magnesium stearate, aluminum stearate, zinc stearate, magnesium ricinoleate, aluminum ricinoleate and/or zinc ricinoleate. Preferably employed vitamins are vitamin A and vitamin E. The skin conditioning agents are applied to the surface of the hydrogel foams, e.g., in the form of a solution or dispersion, e.g., by spraying or dipping the foamed materials into a solution of the skin conditioning agents. After impregnation of the hydrogel foam, the solvent from the active component solutions or dispersions is removed.

To improve the flow behavior, it is also possible to add hydrotropic agents, such as, e.g., ethanol, isopropyl alcohol or polyols to the solution or dispersion containing at least one skin conditioning agent. Polyols which are suitable here preferably have 2 to 15 carbon atoms and at least two hydroxyl groups. Typical examples are glycerol;

alkylene glycols, e.g., ethylene glycol, diethylene glycol, propylene glycol, butylene glycol, hexylene glycol, and polyethylene glycols having an average molecular weight of from 100 to 1000 daltons;

technical grade oligoglycerol mixtures having a degree of self-condensation of from 1.5 to 10, e.g., technical grade diglycerol mixtures with a diglycerol content of from 40 to 50% by weight;

methylol compounds, such as, in particular, trimethylolethane, trimethylolpropane, trimethylolbutane, pentaerythritol and dipentaerythritol;

lower alkylglucosides, in particular those having 1 to 8 carbon atoms in the alkyl radical, e.g., methyl- and butylglucoside;

sugar alcohols having 5 to 12 carbon atoms, e.g., sorbitol or mannitol;

sugars having 5 to 12 carbon atoms, such as, for example, glucose or sucrose;

amino sugars, e.g., glucamine.

Useful skin conditioning agents further include perfume oils and also active components isolated from plants, for example mixtures of natural and synthetic fragrances. Natural fragrances are extracts from flowers (lily, lavender, rose, jasmine, neroli, ylangylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Also suitable are animal raw materials, e.g., civet and castorerum. Typical synthetic fragrance compounds are products of the ester, ether, aldehyde, ketone, alcohol and hydrocarbon type. Fragrance compounds of the ester type are, e.g., benzyl acetate, phenoxyethyl isobutyrate, p-tert-butyleyclohexyl acetate, linalyl acetate, dimethylbenzylcarbinyl acetate, phenylethyl acetate, linalyl benzoate, benzyl formate, ethyl methylphenvlglycinate, allyl cyclohexylpropionate, styrallyl propionate and benzyl salicylate.

The ethers include, e.g., benzyl ethyl ether. The aldehydes include, e.g., the linear alkanals having 8 to 18 carbon atoms, citral, citronellal, citronellyloxyacetaldehyde, cyclamenaldehyde, hydroxycitronellal, lilial and bourgeonal. The ketones include, e.g., the ionones, a-isomethylionone and methyl cedryl ketone. The alcohols include anethole, citronellol, eugenol, isoeugenol, geraniol, linalool, phenylethyl alcohol and terpineol. The hydrocarbons include mainly the terpenes and balsams. Preference is, however, given to using mixtures of different fragrances, which together produce a pleasing scent note. Essential oils of lower volatility, which are mostly used as flavor components, are also suitable as perfume oils, e.g., sage oil, camomile oil, oil of cloves, balm oil, mint oil, cinnamon leaf oil, lime blossom oil, juniperberry oil, vetiver oil, olibanum oil, galbanum oil, labolanum oil, and lavandin oil. Preference is given to using bergamot oil, dihydromyrcenol, lilial, lyral, citronellol, phenylethyl alcohol, α-hexylcinnamaldehyde, geraniol, benzylacetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix Coeur, Iso-E-Super, Fixolide NP, Evernyl, iraldein gamma, phenylacetic acid, geranyl acetate, benzyl acetate, rose oxide, Romillat, Irotyl, and Floramat, alone or in mixtures.

A list of suitable ingredients for skin conditioning agents can be obtained from the CTFA (The Cosmetie, Toiletry and Fragrance Association). From that list more specific examples and more preferable examples can be selected such as allantoin, aluminium hydroxide gel, calamine, cocoa butter, dimethicone, cod liver oil, glycerine, kaolin, petrolatum, lanolin, mineral oil, shark liver oil, white petrolatum, talc, topical starch, zinc acetate, zinc carbonate, zinc oxide, live yeast cell derivatives, aldioxa, aluminum acetate, microporous cellulose, cholecalciferol, colloidal oatmeal, cysteine hydrochloride, dexpanthenol, Peruvean balsam cil, protein hydrolysates, racemic methionine, sodium bicarbonate, vitamin A, buffered mixture of cation and anion exchange resins, corn starch, trolamine, bismuth subnitrate, boric acid, ferric chloride, polyvinylpyrrolidone-vinyl acetate, copolymers, sulfur, tannic acid, and mixtures thereof. When the skin care active ingredient is insoluble, it is dispersed in the composition with a dispersing agent, the dispersing agent may be selected from diethanolamine polyoxyethylene oleyl ether phosphate, polyhydroxystearic acid, polyglyceryl-6 polyricinoleate, neopentyl glycol diisostearate, propylene glycol dicaprate, isoelcosane and polyisobutene and quaternium 18, phenylthiomethylene and quaternium-18 hectorite and triethyl citrate, isohexadecane and quaternium-18 hectorite and propylene carbonate, octyldodecanol and quaternium-18 hectorite and propylene carbonate, mineral oil and quaternium-1,8 hectorite and propylene carbonate, isopropyl myristate and stearalkonium hectorite and propylene carbonate, cyclomethicone and quaternium-18 and SDA 40, lanolin oil, isopropyl palmitate, stearalkonium hectorite, propylene carbonate, propyl paraben, 1-eicosanol, or mixtures thereof. The skin care composition preferably comprises 40-90% of emollient and 10-60% of an agent immobilizing. The emollient may be selected from petroleum-based hydrocarbons, fatty acids, fatty acid esters type, alkyl ethoxylate type, fatty acid ester ethoxylates, fatty alcohol type, polysiloxane type, and mixtures thereof.

The fraction of skin conditioning agents in the solutions or dispersions can be from 1 to 50% and preferably from 5 to 40% by weight.

The open-celled hydrophilic foam formed from crosslinked acid-functional monomers and treated with a skin conditioning agent is in one embodiment of the invention used within the absorbent core. Owing to their remarkable properties, such as liquid acquisition and transmission and also storage, the sheetlike hydrogel foam gradient-postcrosslinked constructs are especially suitable for use as an acquisition and distribution layer or generally completely as an absorbent core.

When used as an absorbent core, the foams described above can perform various functions in hygiene articles, i.e., acquisition, distribution, and storage. The absorbent core can also contain two or more, e.g., 3, 4 or 5, sheetlike constructs of hydrogel foams to be used according to the invention. The individual functions can either be completely performed or be augmented by further constituents, for instance storage can be increased by the addition of superabsorbent granules or acquisition and distribution can be optimized by further cohstituents such as high loft nonwovens, polypropylene nonwovens, polyester nonwovens or chemically modified pulps. Other locations in an absorbent article in which the hydrogel foam with skin conditioning agent may be used are disclosed below.

EXAMPLES

The percentages in the examples are by weight, unless the context suggests otherwise.

Example 1

(a) Preparation of a Foam Film

The following components were mixed in a beaker using a magnetic stirrer:

| | |
|---|---|
| 348.55 g | of acrylic acid (4.84 mol), |
| 135.51 g | of 37.3% sodium acrylate solution in water (0.54 mol), |
| 28.00 g | of polyethylene glycol diacrylate of polyethylene glycol of molar mass 400, |
| 21.33 g | of a 15% aqueous solution of an addition product of 80 mol of ethylene oxide with 1 mol of a linear saturated C16-C18 fatty alcohol, and |
| 65.70 g | of water. |

With ice-cooling, 400.90 g (2.69 mol) of triethanolamine were added to this solution in such a way that the internal temperature did not rise above 16° C. The resulting solution was transferred into a pressure vessel and saturated therein with carbon dioxide under a pressure of 12 bar for 25 min. Under pressure, 26.67 g of a 3% aqueous solution of 2,2'-azobis(2-amidinopropane)dihydrochloride were added and mixed in using a fast stream of carbon dioxide until the mixture was homogeneous. Carbon dioxide was then passed through the reaction mixture for a further 5 min. The saturated reaction mixture was forced under a pressure of 12 bar through a 1 mm diameter nozzle to form a finely celled free-flowing foam.

The monomer foam obtained was placed on an A3 size glass plate having edges 3 mm in height and covered with a second glass plate. The foam sample was irradiated synchronously from both sides with two UV/VIS lamps (Höhnle UV 1000) for 4 minutes.

The foam layer obtained was completely dried in a vacuum oven at 70° C. To determine its properties, a portion of the foam was subsequently adjusted to a moisture content of 5% by spraying with water.

| | |
|---|---|
| Solids content of reaction mixture: | 81.04% |
| Degree of neutralisation: | 60 mole % |
| Monomer foam density: | 0.18 g/cm$^3$ |
| Polymer foam density: | 0.19 g/cm$^3$ |
| Foam structure: | homogeneous, completely open-celled, no skin conditioning agent |
| Thickness of foam film: | 3 mm |

(b) Treatment of the Foam Film with a Skin Conditioning Agent

A foam sample prepared according to example 1(a) in a thickness of 3 mm and measuring 29×20 cm was treated with a 10% commercially available dispersion of Aloe BARBADENSIS Leaf in methanol. The foam thus impregnated was dried at room temperature overnight. The level of Aloe BARBADENSIS Leaf on the foam surface was about 1 g/g.

Example 2

A foam film prepared according to example 1(a) in the dimensions 2.90×200×3 mm was treated with a 5% dispersion of vitamin A in methanol so that the foam film contained >1 g/g of vitamin A absorbed on the surface. The foam sample thus treated was dried at room temperature overnight. When this sample is used, e.g., as an acquisition layer in a hygiene article, a continuous release of vitamin A takes place when the hygiene article is used.

Example 3

Example 2 was repeated with the sole exception that a dispersion of vitamin E was applied to the foam film. When a hygiene article containing a thus finished foam film as, e.g., an acquisition layer is used, a persistant release of vitamin E to the skin takes place.

Example 4

Example 2 was repeated with the sole exception that a 5% dispersion of bisabolol in methanol was used. When a hygiene article containing a thus finished foam film as, e.g., an acquistion layer is used, a persistant release of bisabolol takes place.

Example 5

Example 2 was repeated except that a dispersion of zinc oxide was used. The zinc oxide remained on the surface of the surface of the foam film, which has a skin conditioning effect when used as an acquisition layer in a hygiene article.

Example 6

Use of Skin Conditioning Hydrogel Foams in Absorbent Articles

Hydrogel foams according to the invention may be used in any portion of the article that during use is in contact with the skin of the wearer either directly or through the pervious topsheet. Such portions include the topsheet 2 or part thereof, the elasticised side flaps 10, the barrier flaps, the belts 16 in a belted diaper, the elastic members in the side flaps, barrier flaps and/or waist portion. The hydrogel foam may be used in the form of a sheet or as strips. It may further be applied on a carrier material, e.g., a nonwoven material. This may be made by applying a pre-polymer solution on the carrier material and then initiating polymerisation and foaming to produce the hydrogel foam. Alternatively, a preformed hydrogel foam may be laminated to the carrier material by adhesive or the like.

Hydrogel foams comprising at least one skin conditioning agent may according to one aspect of the invention be used for absorbing body fluids in hygiene articles. Thus, they may be used as an absorbent core or part of an absorbent core in an absorbent article, as has been stated above. As the hydrogel foam gets wet and/or is exposed to pressure the skin conditioning agent contained therein will be gradually released.

The skin condition agents may either be hydrophilic or hydrophobic. Hydrophilic agents will be released from the foam when this is wetted. Hydrophobic skin conditioning agents can be added by means of an oil which is absorbed into the capillaries of the foam. Thus hydrophobic skin conditioning agents will be held in the capillary system of the foam and be released therefrom when the foam is exerted to pressure and/or body heat.

Example 7

Examples of Different Types of Skin Conditioning Agents as Described Above

The hydrogel foam material containing the skin conditioning agent may be located in areas of the article intended to be in contact with at least one of the following body portions of the wearer: groins, buttocks, genitalia, hips. These are portions of the body where skin irritation most frequently occurs. Such skin irritation may be caused by abrasion, heat, moisture, pressure, etc. The hydrogel foam has a smooth and somewhat slippery surface, thus making it a low friction against the skin of the wearer. This makes it suitable to use in locations of the article where abrasion against the skin most frequently will occur, especially groins, buttocks and hips. Other body parts that are inherently sensitive to irritation are scrotum and mucous membranes. Belts in belted diapers may also cause skin irritation, and the hydrogel foam material is therefore suited to use on the inside 16a of the belt 16 intended to be in contact with the skin of the wearer.

FIG. 2 illustrates a hydrogel foam material used under the topsheet 2 as a liquid acquisition layer 9. It is further illustrated that strips 19 of hydrogel foam material are applied on the body contacting distal edge 14 of the elastic barrier flaps 12. Strips 20 of hydrogel foam material are further applied on the body contacting surface of the elasticised side flaps 10.

The hydrogel foam is further elastic to some degree and is therefore suited to be used as or constitute part of elastic members in the article, such as leg elastics, waist elastics, elastic leakage barrier cuffs, etc. Absorbent articles containing many elastic members are pant diapers, and the hydrogel foam material may therefore advantageously be used in such articles. As the hydrogel swells upon contact with liquid the sealing effect against leakage will be even improved.

Strips of hydrogel foam may further be used as a feces barrier in an absorbent article, preventing feces from being displaced towards the front part of the diaper. The swelling of the hydrogel improves the sealing effect. When used as a feces barrier, the hydrogel foam may advantageously contain enzyme inhibitors, e.g., metal salts of iron or zinc, trace amounts of heavy metal ions such as copper or silver, ethylene diamine tetraacetic acid (EDTA), soybean trypsin inhibitor, lime bean protease inhibitor, maize protease inhibitor, stearylglycyrrhetinate, glycerol triacetate, betaine compounds, sulphobetaine compounds, cholestyramine, and p-guanidinobenzoates.

The hydrogel foam further is resiliently compressible and thus pressure relieving, which makes it suitable to use in locations of the article where pressure against the body will occur most frequently, such as buttocks and hips, thus preventing the occurrence of pressure sores.

The hydrogel foam may additionally be treated so as to enhance the wet strength. This may be made, e.g., by treating the foam with a polymer containing primary and/or secondary amino groups, e.g., polymers containing vinylamine units, polyethylene imines, polyvinyl guanidine, lysine condensates and/or polyallyl amine.

The above-described embodiments are merely illustrative and are in no way intended to limit the present invention.

What is claimed is:

1. An absorbent article comprising:
A liquid permeable topsheet,
A liquid impermeable backsheet,
an absorbent body enclosed therebetween, a hydrogel foam made from a hydrogel material to be applied in contact with the skin of a wearer during use, and a skin conditioning agent contained in the hydrogel foam to be applied in skin contact with the wearer in such a manner that the skin conditioning agent is transferable to the skin when the hydrogel foam is applied in contact with skin, wherein the hydrogel foam contains between 5 and 95% by weight skin conditioning agent, calculated on the combined weight of hydrogel foam and skin conditioning agent, wherein the hydrogel foam containing the skin conditioning agent forms part of or constitutes an elastic member in the article.

2. An absorbent article comprising:
A liquid permeable topsheet,
A liquid impermeable backsheet,
an absorbent body enclosed therebetween,
a hydrogel foam made from a hydrogel material to be applied in contact with the skin of a wearer during use, and a skin conditioning agent contained in the hydrogel foam to be applied in skin contact with the wearer in such a manner that the skin conditioning agent is transferable to the skin when the hydrogel foam is applied in contact with skin, wherein the hydrogel foam contains between 5 and 95% by weight skin conditioning agent, calculated on the combined weight of hydrogel foam and skin conditioning agent, wherein the hydrogel foam is applied on a body-contacting surface of a belt on a diaper.

3. An absorbent article comprising:
A liquid permeable topsheet,
A liquid impermeable backsheet,
an absorbent body enclosed therebetween,
a hydrogel foam made from a hydrogel material to be applied in contact with the skin of a wearer during use, and a skin conditioning agent contained in the hydrogel foam to be applied in skin contact with the wearer in such a manner that the skin conditioning agent is transferable to the skin when the hydrogel foam is applied in contact with skin, wherein the hydrogel foam contains between 5 and 95% by weight skin conditioning agent, calculated on the combined weight of hydrogel foam and skin conditioning agent, wherein the hydrogel foam is applied as strips to create leakage barriers in the article.

4. An absorbent article comprising:
a liquid permeable topsheet,
a liquid impermeable backsheet,
an absorbent body enclosed therebetween,
a hydrogel foam made from a hydrogel material to be applied in contact with the skin of a wearer during use, and a skin conditioning agent contained in the hydrogel foam to be applied in skin contact with the wearer in such a manner that the skin conditioning agent is transferable to the skin when the hydrogel foam is applied in contact with the skin, wherein the hydrogel foam contains between 5 and 95% by weight skin conditioning agent, calculated on the combined weight of hydrogel foam and skin conditioning agent, wherein the skin conditioning agent comprises an emollient, wherein the emollient is selected from a group consisting of petroleum-based hydrocarbons, fatty acids, fatty acid esters, alkyl ethoxylates, fatty acid ester ethoxylates, fatty alcohols, polysiloxanes, and mixtures thereof.

5. An absorbent article comprising:
A liquid permeable topsheet,
A liquid impermeable backsheet,
an absorbent body enclosed therebetween,
a hydrogel foam made from a hydrogel material to be applied in contact with the skin of a wearer during use, and a skin conditioning agent contained in the hydrogel foam to be applied in skin contact with the wearer in such a manner that the skin conditioning agent is transferable to the skin when the hydrogel foam is applied in contact with skin, wherein the hydrogel foam contains between 5 and 95% by weight skin conditioning agent, calculated on the combined weight of hydrogel foam and skin conditioning agent, wherein the emollient is a fatty acid.

* * * * *